(12) United States Patent
White et al.

(10) Patent No.: US 12,109,358 B2
(45) Date of Patent: Oct. 8, 2024

(54) SYSTEM AND METHOD FOR STIMULATING AIRWAYS

(71) Applicant: AUT VENTURES LIMITED, Aukland (NZ)

(72) Inventors: David Edward White, Aukland (NZ); Thomas George McLeod, Aukland (NZ)

(73) Assignee: AUT VENTURES LIMITED, Auckland (NZ)

( * ) Notice: Subject to any disclaimer, the term of this patent is extended or adjusted under 35 U.S.C. 154(b) by 0 days.

(21) Appl. No.: 17/905,071

(22) PCT Filed: Feb. 26, 2021

(86) PCT No.: PCT/NZ2021/050029
§ 371 (c)(1),
(2) Date: Aug. 26, 2022

(87) PCT Pub. No.: WO2021/173014
PCT Pub. Date: Sep. 2, 2021

(65) Prior Publication Data
US 2023/0138935 A1    May 4, 2023

(30) Foreign Application Priority Data
Feb. 26, 2020    (NZ) .................................... 762123

(51) Int. Cl.
*A61M 16/06*    (2006.01)
*A61M 16/00*    (2006.01)

(52) U.S. Cl.
CPC .... *A61M 16/0006* (2014.02); *A61M 16/0666* (2013.01)

(58) Field of Classification Search
CPC .......... A61M 16/0051; A61M 16/0066; A61M 16/0069; A61M 16/0096; A61M 16/022;
(Continued)

(56) References Cited

U.S. PATENT DOCUMENTS 6,708,690 B1 *  3/2004  Hete .................. A61M 16/0096
                                                                128/205.24
9,486,599 B2 * 11/2016  Schaetzl ........... A61M 16/0666
(Continued)

FOREIGN PATENT DOCUMENTS

| WO | 2011141841 A1 | 11/2011 |
| WO | 2017187390 A1 | 11/2017 |
| WO | 2019140333 A1 | 7/2019 |

OTHER PUBLICATIONS

Schweitzer, John (Authorized Officer), International Search Report and Written Opinion dated May 3, 2021, International Application No. PCT/NZ2021/050029, 4 pages.
(Continued)

*Primary Examiner* — Annette Dixon
(74) *Attorney, Agent, or Firm* — MH2 TECHNOLOGY LAW GROUP, LLP

(57) ABSTRACT

Described is a method of stimulating airways of a mammal comprising: cyclically occluding a nasal air stream at a frequency rate between 50 Hz to 650 Hz. Also described is an apparatus for stimulating airways of a mammal, comprising: a fluid connection to each of a first and second naris of the mammal; and an occluding device configured to cyclically occlude a nasal air stream within each fluid connection at a frequency rate between 100 Hz to 650 Hz.

28 Claims, 15 Drawing Sheets

(58) Field of Classification Search
CPC ............ A61M 16/024; A61M 16/0493; A61M 16/0666; A61M 16/0683; A61M 16/10; A61M 16/107; A61M 16/109; A61M 16/16; A61M 16/161; A61M 16/202; A61M 16/208; A61M 2016/0021; A61M 2016/0027; A61M 2016/003; A61M 2016/0036; A61M 2016/0039; A61M 2202/0007; A61M 2202/0208; A61M 2202/03; A61M 2205/12; A61M 2205/15; A61M 2205/3365; A61M 2205/3375; A61M 2205/3673; A61M 2205/42; A61M 2205/50; A61M 2205/581; A61M 2205/587; A61M 2205/8206; A61M 2205/8237; A61M 2230/46; A61M 2230/50; F04D 17/16; F04D 27/001; F04D 29/4246

See application file for complete search history.

(56) References Cited

U.S. PATENT DOCUMENTS

| | | |
|---|---|---|
| 2005/0051174 A1 | 3/2005 | Emerson |
| 2006/0169281 A1* | 8/2006 | Aylsworth ........ A61M 16/0666 128/204.26 |
| 2006/0174885 A1* | 8/2006 | Aylsworth ............ A61M 16/10 128/207.18 |
| 2008/0216835 A1* | 9/2008 | McGinnis ........... A61M 16/161 128/204.23 |
| 2010/0122699 A1 | 5/2010 | Birnkrant |
| 2012/0247466 A1 | 10/2012 | Avni |
| 2013/0319416 A1 | 12/2013 | Brown et al. |
| 2015/0165144 A1 | 6/2015 | Lee et al. |
| 2016/0193438 A1 | 7/2016 | White et al. |
| 2017/0087317 A1 | 3/2017 | Peesay et al. |
| 2017/0296767 A1 | 10/2017 | White et al. |
| 2019/0160240 A1* | 5/2019 | Bothma .............. F04D 29/4246 |
| 2019/0262559 A1 | 8/2019 | Bogan et al. |
| 2021/0220586 A1* | 7/2021 | Shah ..................... A61M 11/00 |

OTHER PUBLICATIONS

Extended European Search Report dated May 24, 2024 in counterpart European Application No. 21760851 (6 pages).

* cited by examiner

SYSTEM AND METHOD FOR STIMULATING AIRWAYS

FIELD

This invention relates to a system and method for stimulating airways.

BACKGROUND

Up to 25% of the world's population is thought to be negatively affected by nasal congestion, a condition of increased breathing resistance often described as 'stuffiness' (R1). Nasal congestion is a common symptom of upper airway disorders and is associated with a range of causes (R2). Variable nasal congestion is usually caused by reversible and potentially spontaneously resolving causes such as mucosal inflammation and nasal secretions found during nasal allergy or upper respiratory infection (R1).

Normal tidal nasal breathing air flow exert fluctuating pressure and shear stresses against the airway mucosa, stimulating the discharge of airway surface liquid and mucociliary transport via cellular purinergic channels (R3). This mechano-stimulation aids in the regulation and enhancement of mammal airway defence (R4).

The paranasal sinuses are a rich endogenous source of nitric oxide (NO) gas (R5) which has been shown to protect and treat bacterial, fungal and viral airway infections, and stimulate mucociliary clearance of entrapped pathogens (R6). NO is considered crucial in airway defence and thought to play an important role in nasal airway resistance, with higher levels of NO being associated with nasal decongestion (R7). This positive association between nasal NO concentration and nasal decongestion has been demonstrated by humming which greatly increases the concentration of inhaled endogenous nitric oxide (R8, R9) while also leading to a reduction in nasal congestion (R10). Humming is thought to also provide additional mechano-stimulation of the airway mucosa purinergic channels, increasing airway hydration and mucociliary transport.

NO is a free radical gas signalling molecule which is also produced throughout the human body that plays a variety of important roles. These include assisting oxygen uptake in the lungs, improving circulation through vasodilation, modulating neurological function including depression, memory (R11) and sleep staging, and a variety of other important signalling activities. To maintain good health the concentration of NO needs to remain within certain limits. Low NO levels are associated with poor wellbeing and closely linked to reduced sleep quality (R12) and interruption to the sleep/wake cycle (R13). Low levels of circulating NO are also associated with high blood pressure, poor circulation, low blood oxygen saturation levels, muscle pain and is linked to many long-terms ailments, such as chronic obstructive pulmonary disease (COPD). Smoking, stress, injury, pathology, poor lifestyle choices, as well as nasal abnormalities and aging can lead to a reduction in circulating NO levels. This reduction is linked to an increased risk of cardiovascular disease, poor metabolic disease management, poor circulation and insomnia. High levels of NO are thought to potentially reduce asthma and airway viral infections (R14), COPD (R15), rhinovirus (R16), ischemic stroke and traumatic brain injury (R13).

The human paranasal sinuses, including the maxillary sinuses, contain the highest levels of NO found in the body (R17, R18) so unsurprisingly respiratory physiotherapists recommend nasal breathing over mouth breathing for many reasons including the augmentation of inhaled nitric oxide (iNO) (R19). During normal nasal breathing iNO is metered into the inhaled air before passing into the lungs where it assists oxygen uptake before becoming dissolved into the blood to then circulate throughout the body. Many benefits of nasal breathing and augmented iNO level are claimed including prevention and protection from airway infection (R20) through to its role in modulating healthy pulmonary function (R21).

NO is considered to be crucial in airway defence (R17, R18, R20) and thought to play an important role in nasal airway resistance, with higher levels of NO being associated with nasal decongestion (R7). This positive association between nasal NO concentration and nasal decongestion has been demonstrated by humming which greatly increases the concentration of inhaled endogenous nitric oxide (R8, R9) while also leading to a reduction in nasal congestion (R48).

The status of the nasal cycle, where one nostril normally conducts more tidal airflow, termed 'patent', compared to the other, termed 'congested', has previously been shown to allow the nose to simultaneously undertaking its air-conditioning and mucociliary roles (R22). A healthy nasal cycle also enables the nose to act as a NO regenerator to maintain a higher mean concentration of iNO compared to a non-cycling nose. This is realised through the NO concentration within the paranasal sinuses on the congested side of the nose increasing as a result of low airflow whereas the NO concentration on the patent side paranasal sinuses are progressively depleted due to the higher airflow. Normal periodic change in the nasal cycle status results in the previously congested airway paranasal sinuses now having available a high concentration of stored NO so when this side of the nose becomes patent (where it conducts the majority of the tidal nasal airflow) there is a high concentration store of NO available to be inhaled. Conversely, the NO storage levels in the previously patent side of the nose, depleted due to the previously higher airflow, start to increase again due to the reduction in airflow when this side becomes congested. FIG. 1 shows how this nasal cycle NO regeneration effect enables a higher mean level of maximum iNO concentration 170 to be entrained into the lungs compared to the case of the of maximum iNO concentration 270 where there was no nasal cycle, shown by FIG. 2, and the maximum iNO concentration 370 when near equal airflow passes down both nasal airways, such as that found during pressurised nasal breathing (R23), shown by FIG. 3.

In FIGS. 1 to 3, the graphs 100, 200, 300 show internasal airflow apportionment, graphs 130, 230, 330 show paranasal sinus NO concentration (ppb) and graphs 160, 260, 360 show and maximum iNO concentration. Time 105, 135, 165, 205, 235, 265, 305, 335, 365 is shown on the x-axis. The y-axis shows internasal airflow apportionment (108, 208, 308), paranasal sinus NO concentration (ppb) (138, 238, 338) and maximum iNO concentration (ppb) (168, 268, 368). Lines 110, 210, 310 show the percentage of internasal airflow through the left nostril, lines 120, 220, 320 show the percentage of internasal airflow through the right nostril. Lines 140, 240, 340 show the paranasal sinus NO concentration in the left sinus and lines 150, 250, 350 shows the paranasal sinus NO concentration in the right sinus. Lines 170, 270, 370 show the mean of maximum iNO concentration.

The human autonomic nervous system (ANS) undertakes the unconscious regulation of many body functions associated with the ongoing maintenance of maintaining life (homeostasis) and is closely associated with the hormonal and the immunological systems (R24). The two main branches of the ANS, sympathetic and parasympathetic, jointly regulate a multitude of organ, immune and regulatory systems and have opposing affect. Through brain to body signalling (efference), these two branches periodically alternate in dominance so that the organs and systems they regulate operate between two states; sympathetic dominance 'fight or flight' (stressed) or parasympathetic dominance, rest and digest' (relaxed). Heart rate, blood pressure, alertness, energy levels, blood flows and insulin levels (R25), hunger and digestion, organ activity, hormone release (R26), stress levels (cortisol and adrenaline hormone release), cognitive function, sleep stage, and many more life sustaining functions are all linked to this constant cycling of ANS state dominance that continue throughout the day and night (R24). The ANS system also receives feedback signals from the external environment and physical body (afference) that can change the state of ANS dominance to aid survival and wellbeing. These signals, for example a loud explosion, could change the ANS dominance from parasympathetic (rest & digest) to sympathetic (fight or flight). This change would trigger the release of stress hormones, such as adrenaline and cortisol, and enable more oxygen and blood sugar to be available to the muscles to enable the individual to flee the perceived risk to life.

Healthy ANS cyclic regulation is termed 'sympathovagal balance', where there is normal distribution of cycling of the ANS between sympathetic and parasympathetic dominant states throughout the day and night. This periodic cycling was first associated with the changing states of the ANS in 1954 by Hess who described the cycling variation in autonomic function between 'energy' and 'restitution' states (R26). Later, in 1960, sleep researcher Nathaniel Kleitmann proposed the human body operated on a basic-rest-activity cycle (BRAC), where it alternated between activities associated with activity or rest (R26, R27). This hypothesis proposed these contrasting ultradian (sub 24 hour) ANS cycles occur in varying degrees of dominance and duration during both waking and sleep, as demonstrated by periods of activity or rest during waking and rapid eye movement (REM) and non-REM staging during sleep.

Over exposure to sources of stress, such as excessive caffeine intake, late nights, shift work, relationship breakdown, physical trauma and exposure to other forms of excessive ANS stimuli sends a signal back to the brain (afference) that may, if sustained long-term, cause sympathetic over-stimulation and lead to disruption of an individual's sympathovagal balance (R24). This ANS dysfunction can potentially lead to poor wellbeing, and if persisting longer term, cause chronic disease, cancer, neurological disorder and early morbidity (R24). Autonomic nervous system dysfunction is thought to precede many illnesses and diseases including cardiovascular and metabolic diseases including Type 2 diabetes (R25, R28).

The positive effect regulated nostril breathing, commonly known as yoga breathing, has on the ANS has been well published which includes change in heart rate variability (HRV) and cardiovascular risk (R29), cognitive performance (R30), psychiatry treatment (R31) and post stroke language, spatial abilities and anxiety (R32). While the mechanism(s) by which regulated nostril breathing can influence the ANS are poorly understood, iNO is thought to play a major role given NO is known to decrease ANS sympathetic over-excitation (stress) (R33). This change could then affect the ANS sympathetic/parasympathetic balance and potentially restore sympathovagal balance.

The status of the nasal cycle, where one nostril normally conducts more tidal airflow compared to the other, has been closely linked to sleep stage(R34) and has previously been used to indicate the status of ANS dominance during waking and sleep (R35, R36). Here the left or right nostril airflow dominance indicates parasympathetic or sympathetic dominance respectively (R31, R37). Previous work has shown the afference signalling influence of regulated nostril breathing (yogic breathing) on the state of ANS dominance (R31, R38, R39) with the right and left nostril influencing sympathovagal balance, heart rate variability and cardiovascular risks (R29) and metabolism (R40). Unilateral forced nostril breathing (UFNB) through the right nostril is associated with ANS sympathetic dominance (stressed) while UFNB through the left nostril is associated with ANS parasympathetic (relaxed) dominance (R31). Abnormal or total lack of patterns of nasal cycling have also been found in studies of neurological disorders and disease (R38, R41, R42), and many other chronic disease states (R43). This associations is suggestive that reduction in iNO levels may play an early role in the development of many neurological and chronic diseases since it serves to suppress ANS sympathetic over-excitation (stress response).

Studies have demonstrated that humming at a range of frequencies spanning approximately 100 Hz to 450 Hz augments levels of exhaled NO by up to 15 times the normal value (R44-R46). During humming, augmented NO release from the paranasal sinuses is achieved through slight pressure variations over a broad frequency range, spanning approximately 100 Hz to 450 Hz. While this technique has been shown to rapidly resolve chronic rhinosinusitus (R47) within the nasal cavity, the additional NO does not enter the lower airways as the individual is exhaling during the humming manoeuvre.

PCT Application No. PCT/NZ2015/050169 A METHOD AND APPARATUS FOR THE CONTROLLED DELIVERY OF GASES which describes controlling the cycling of the naris is incorporated by reference in full.

SUMMARY

According to one example embodiment there is provided a method of stimulating airways of a mammal comprising:
cyclically occluding a nasal air stream at a frequency rate between 50 Hz to 650 Hz.

Preferably stimulating the airways of a mammal improves nasal airflow by decongesting nasal obstruction in the mammal.

Preferably stimulating the airways of a mammal improves airway infection by enhancing airway hydration and mucociliary transport.

Preferably stimulating the airways of a mammal improves the inhaled Nitric Oxide in the mammal.

Preferably the mammal has two nares, a first naris and a second naris and cyclically occluding the nasal air stream comprises simultaneously cyclically occluding the nasal air stream of both nares.

Preferably the mammal has two nares, a first naris and a second naris and during a first mode cyclically occluding the nasal air stream comprises cyclically occluding only the nasal air stream of the first naris.

Preferably the nasal air stream to the second naris is unrestricted.

Preferably the nasal air stream to the second naris is restricted.

Preferably the restriction is partial.

Preferably the during the first mode the first naris is the congested naris and the second naris is the patent naris.

Preferably during a second mode cyclically occluding the nasal air stream comprises cyclically occluding only the nasal air stream of the second naris.

Preferably the nasal air stream to the second naris is unrestricted.

Alternatively, the nasal air stream to the second naris is restricted.

Preferably the restriction is partial.

Preferably during the second mode the second naris is the congested naris and the first naris is the patent naris.

Preferably the change between the first mode and the second mode is controlled by a controller.

Preferably the period of operation of the first mode or the second mode is between 1 and 360 minutes, preferably between 1 and 15 minutes, more preferably between 1 and 5 minutes.

Preferably the nasal air stream is cyclically occluded during both inhalation and exhalation.

Preferably the nasal air stream is cyclically occluded during inhalation only.

Preferably including controlling the occlusion by controlling an average percentage of obstruction of the nasal air stream.

Preferably the average percentage of obstruction is between 5 and 95 percent.

Preferably controlling the average percentage of obstruction of the nasal air stream includes controlling a percentage of time in a cycle in which the nasal air stream is at least partial obstructed and controlling a maximum percentage of obstruction of the nasal air stream.

Preferably the maximum percentage of obstruction of the nasal air stream is between 5 and 95 percent.

Preferably the frequency rate is between 100 Hz to 450 Hz.

Preferably the mammal is a human.

According to a further example embodiment there is provided an apparatus for stimulating airways of a mammal, comprising:
- a fluid connection to each of a first and second naris of the mammal; and
- an occluding device configured to cyclically occlude a nasal air stream within each fluid connection at a frequency rate between 100 Hz to 650 Hz.

Preferably stimulating the airways of a mammal improves the inhaled Nitric Oxide in the mammal.

Preferably stimulating the airways of a mammal improves airway infection by enhancing airway hydration and/or mucociliary transport.

Preferably stimulating the airways of a mammal improves nasal airflow by decongesting nasal obstruction in the mammal.

Preferably cyclically occluding the nasal air stream comprises simultaneously cyclically occluding the nasal air stream of both nares.

Preferably the apparatus in a first mode cyclically occludes only the nasal air stream of the first naris.

Preferably in the first mode the nasal air stream to the second naris is unrestricted.

Alternatively, in the first mode the nasal air stream to the second naris is restricted.

Preferably the restriction is partial.

Preferably in the first mode the first naris is the congested naris and the second naris is the patent naris.

Preferably the apparatus in a second mode cyclically occludes only the nasal air stream of the second naris.

Preferably in the second mode the nasal air stream to the second naris is unrestricted.

Alternatively, in the second mode the nasal air stream to the second naris is restricted.

Preferably the restriction is partial.

Preferably wherein in the second mode the second naris is the congested naris and the first naris is the patent naris.

Preferably the change between the first mode and the second mode is controlled by a controller.

Preferably the period of operation of the first mode or the second mode is between 1 and 360 minutes, preferably between 1 and 15 minutes, more preferably between 1 and 5 minutes.

Preferably the nasal air stream is cyclically occluded during both inhalation and exhalation.

Preferably wherein the nasal air stream is cyclically occluded during inhalation only.

Preferably the apparatus including controlling the occlusion by controlling an average percentage of obstruction of the nasal air stream.

Preferably the average percentage of obstruction is between 5 and 95 percent.

Preferably controlling the average percentage of obstruction of the nasal air stream includes controlling a percentage of time in a cycle in which the nasal air stream is at least partial obstructed and controlling a maximum percentage of obstruction of the nasal air stream.

Preferably the maximum percentage of obstruction of the nasal air stream is between 5 and 95 percent.

Preferably the frequency rate is between 100 Hz to 450 Hz.

Preferably the mammal is a human.

Preferably further including a flow direction sensor.

Preferably the apparatus further includes a pressure sensor.

Preferably the apparatus includes a battery and is configured to be worn under the nose.

Preferably the apparatus is a standalone device.

Preferably the apparatus further comprises an air supply device.

Preferably the air supply device is selected from the group comprising CPAP, Bi-PAP, Auto-PAP and other assisted breathing devices.

Preferably the occluding device is a linear slide shutter system including a liner solenoid actuator.

Alternatively, the occluding device is a linear shutter system with crank actuator.

Alternatively, the occluding device is a rotating shutter system.

Alternatively, the occluding device is a transverse rotating partially blocking shutter inline in the fluid connection.

Preferably the transverse rotating partially blocking shutter is a barrel and the barrel include cut outs.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which.

DETAILED DESCRIPTION

FIGS. 4 to 11 and 13 to 22 illustrates various shutter systems and an example apparatus according to various example embodiments.

Figure 1:
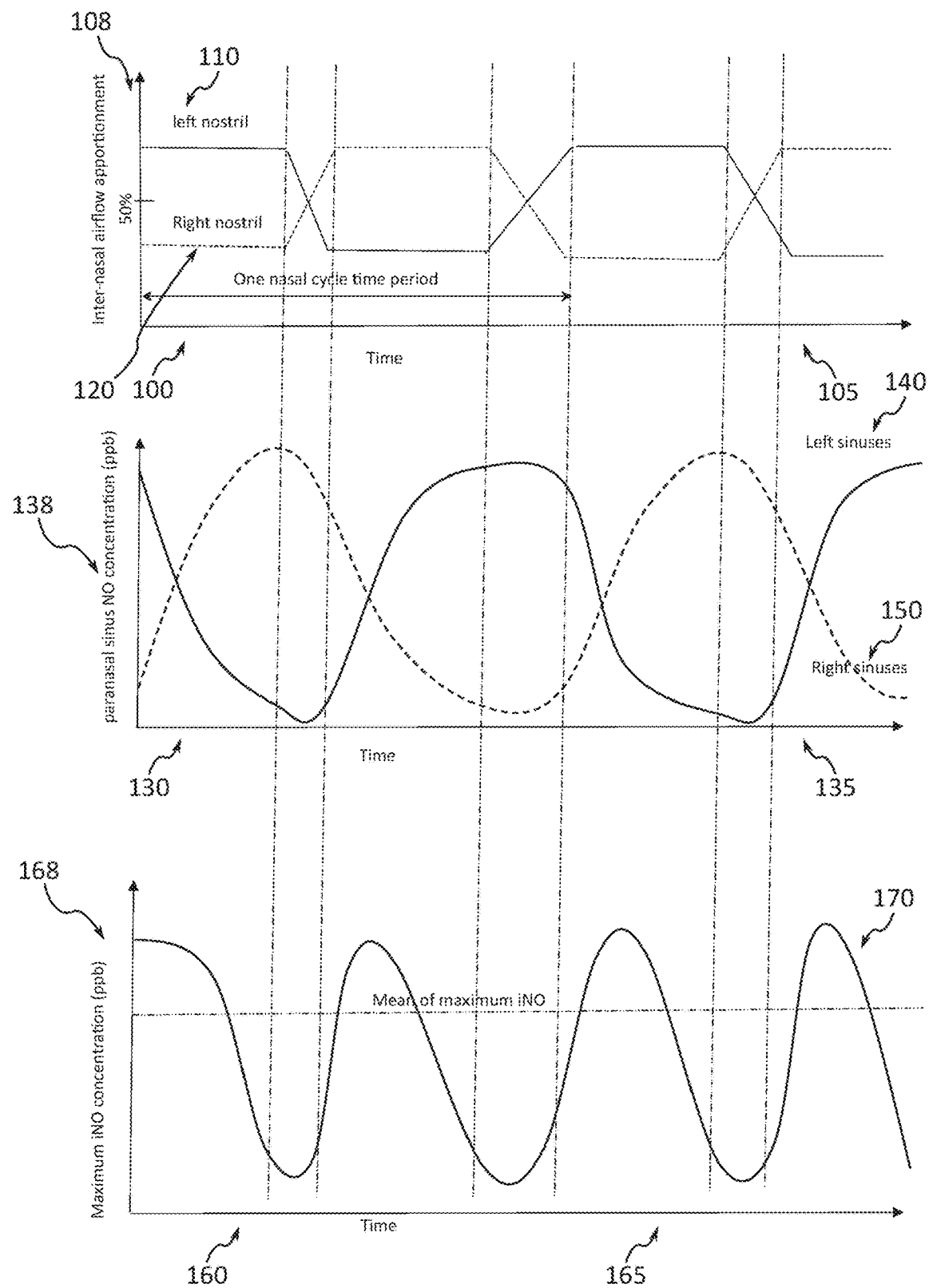
FIG. 1 is a graph illustrating paranasal and iNO concentrations during normal nasal cycling.
Figure 2:
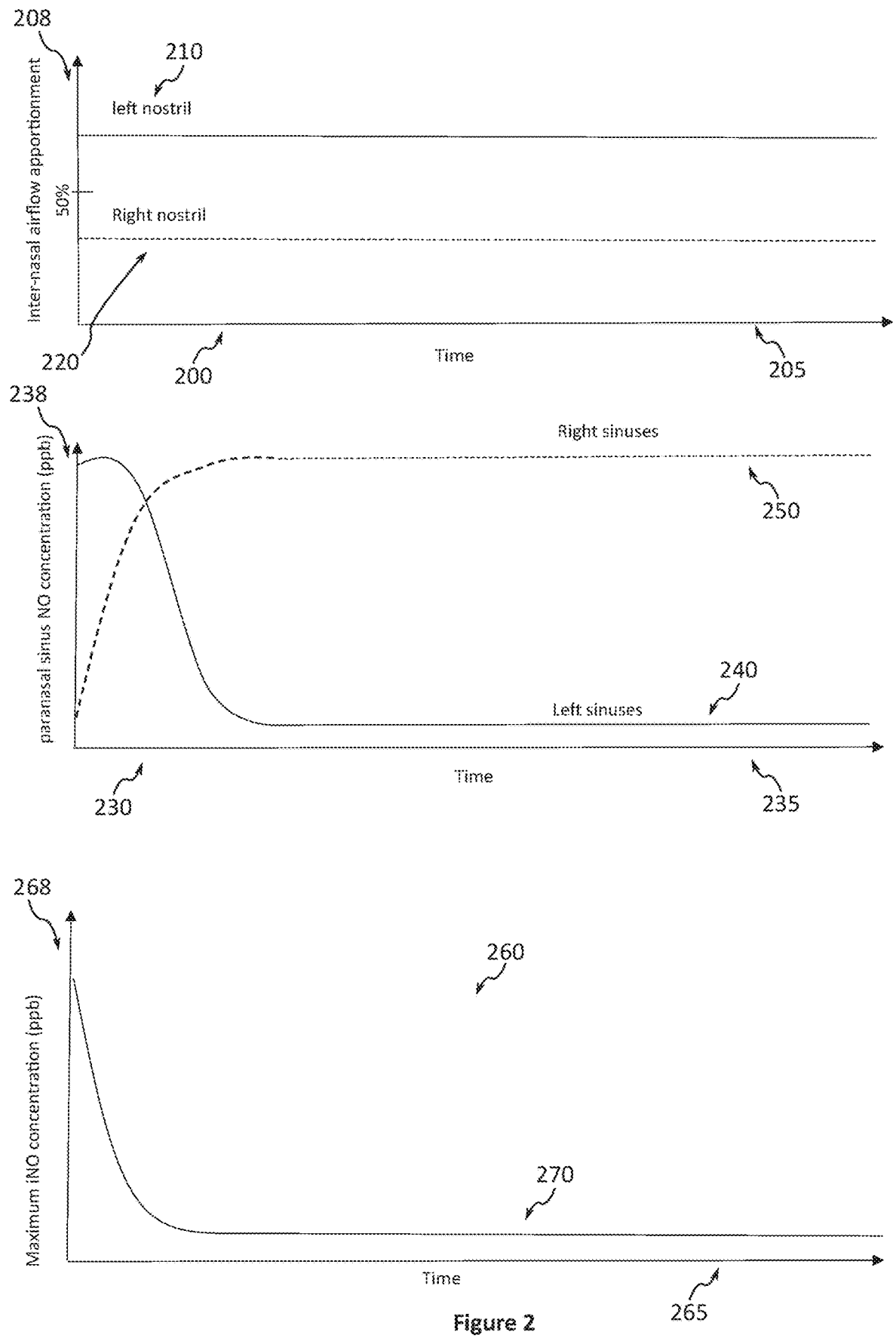
FIG. 2 is a graph illustrating paranasal and iNO concentrations during absence of nasal cycling.
Figure 3:
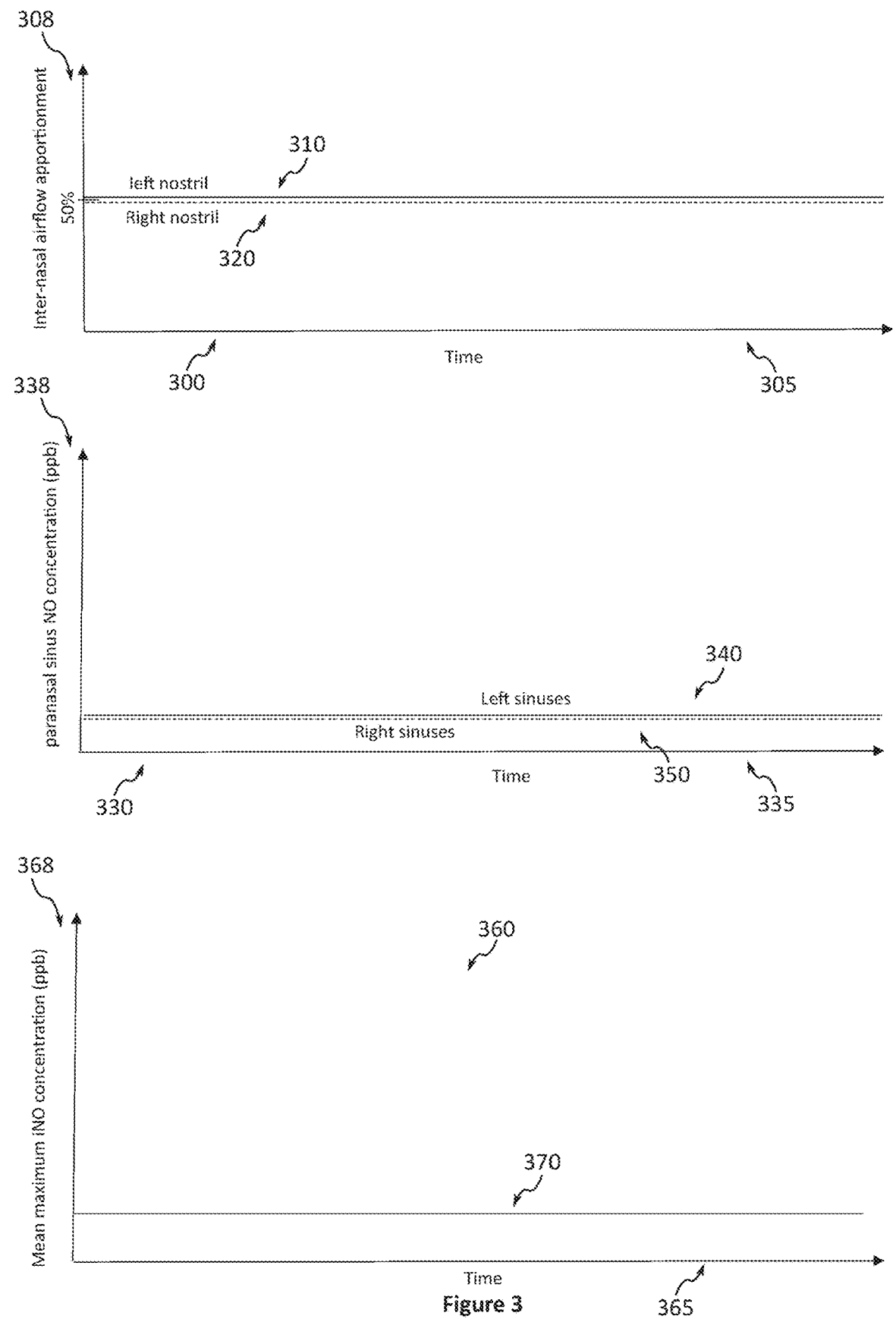
FIG. 3 is a graph illustrating paranasal and iNO concentrations during sustained equal internasal airflow apportionment.
Figure 4:
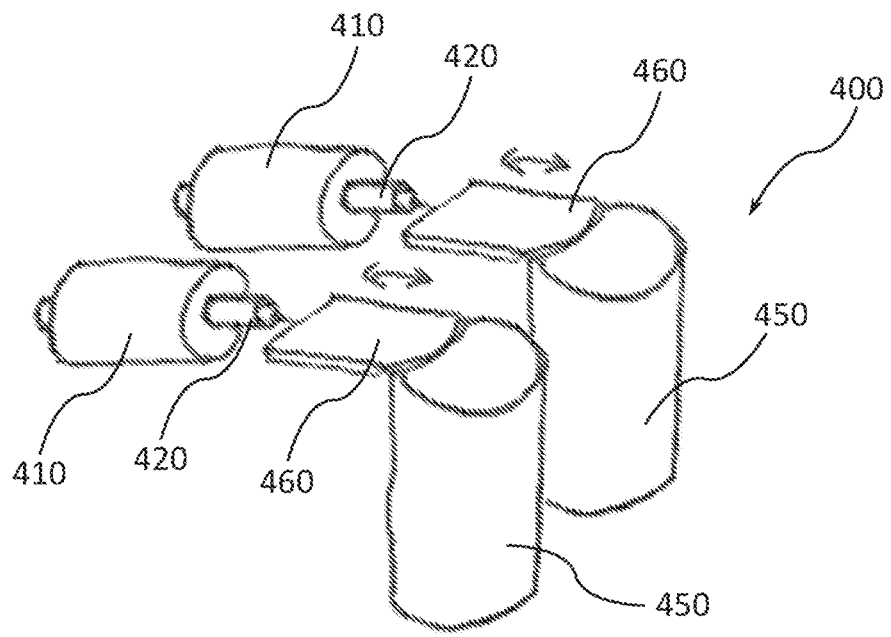
FIG. 4 is an example embodiment of a linear slide shutter system with a liner solenoid actuator.

The linear slide shutter system 400 illustrated in FIG. 4, delivers pressure oscillations into the inhaled air stream path 450 entering the nose to elevate the levels of iNO and/or provide mechanical stimulation to the airway mucosa. In one embodiment this is realised by using an airflow interrupter 460, such as air airflow shutter, that cyclically partially occludes the incoming air stream at a frequency rate replicating that found during low-frequency humming (100 Hz to 650 Hz, preferably 100 Hz to 450 Hz). Motors 410 are connected to the airflow interrupters 460 using linear actuators 420. The motors 410 move the airflow interrupters 460 backwards and forwards in a linear motion to partially occlude the incoming air stream.

FIGS. 4 though to 11 and 13 to 16 illustrate various potential embodiments of airflow shuttering systems. Other embodiments that occlude the incoming air stream at a frequency rate replicating that found during low-frequency humming (100 Hz to 650 Hz, preferably 100 Hz to 450 Hz) may also be used.

Figure 5:
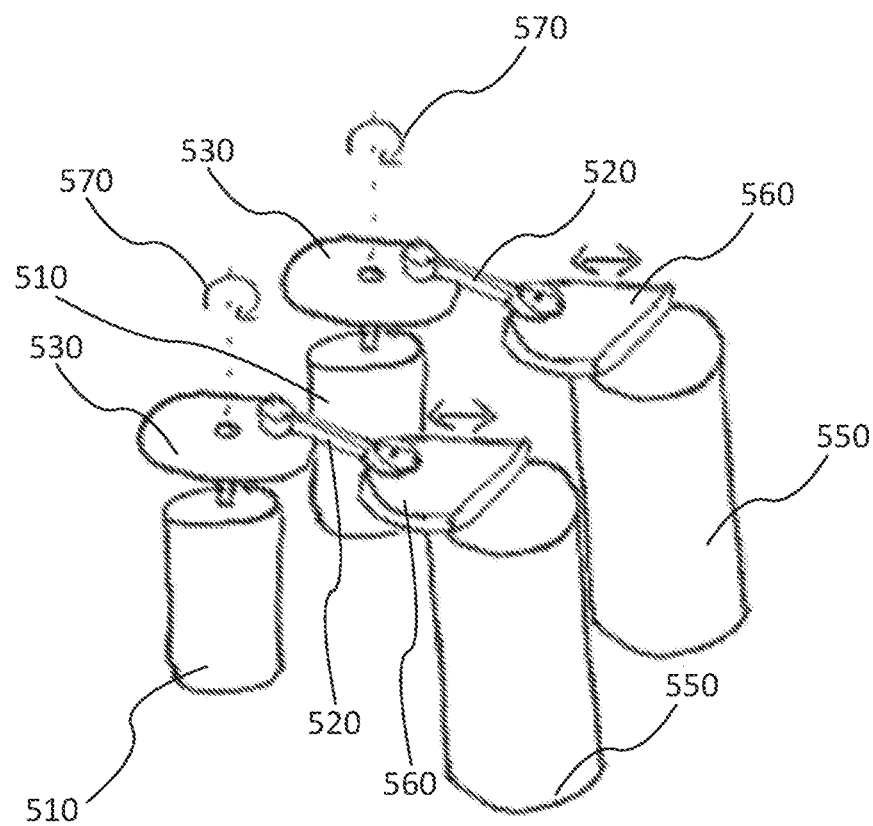
FIG. 5 is an example embodiment of a slide linear shutter system with a crank actuator.

Referring to FIG. 5 motors 510 are connected to the airflow interrupters 560 using rotating 570 disks 530, that are in turn connected to a link 520. The disks 530 and link 520 provide a linear motion to the airflow interrupter 560. The motors 510 move the airflow interrupters 560 backwards and forwards in a linear motion to partially occlude the incoming air stream in the air stream path 550.

Figure 6:
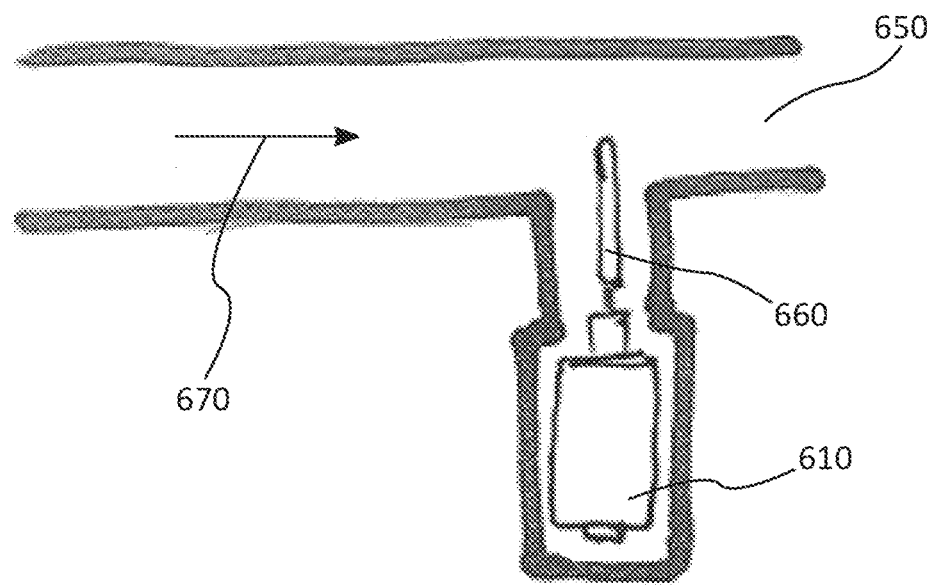
FIG. 6 is a side view of an example embodiment of a linear shutter system.

Referring to FIG. 6 a motor 610 is connected to an airflow interrupter 660. The motor 610 moves the airflow interrupter 660 backwards and forwards in a linear motion to partially occlude the incoming air stream 670 in the air stream path 650.

Figure 7:
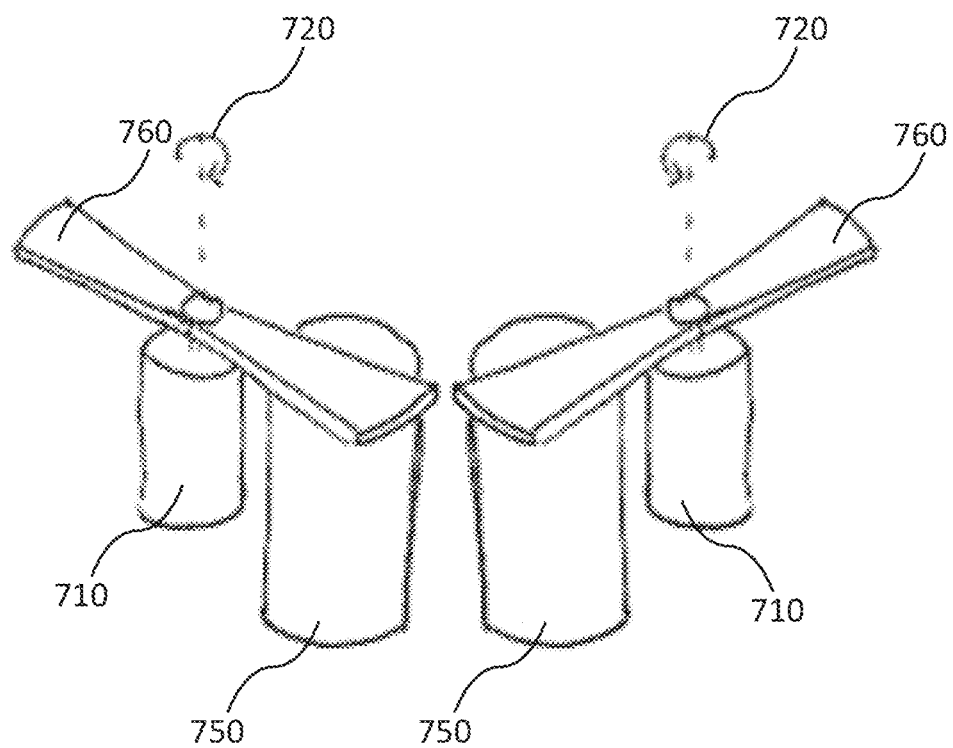
FIG. 7 is an example embodiment of a rotating shutter system with a motor actuator.

Referring to FIG. 7 motors 710 are connected to airflow interrupters 760. The motors 710 rotate 720 airflow interrupters 770 in a circular motion to partially occlude the incoming air stream in the air stream path 750.

Figure 8:
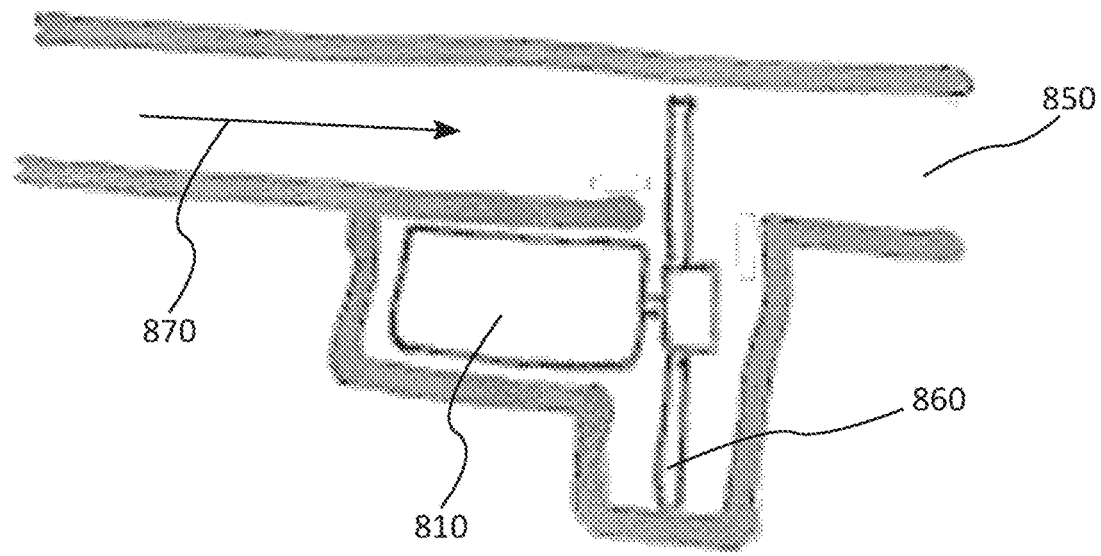
FIG. 8 is a side view of an example embodiment of a rotating shutter system.

Referring to FIG. 8 a motor 810 is connected to an airflow interrupter 860. The motor 810 rotates the airflow interrupters 860 in a circular motion to partially occlude the incoming air stream 870 in the air stream path 850.

Figure 9:
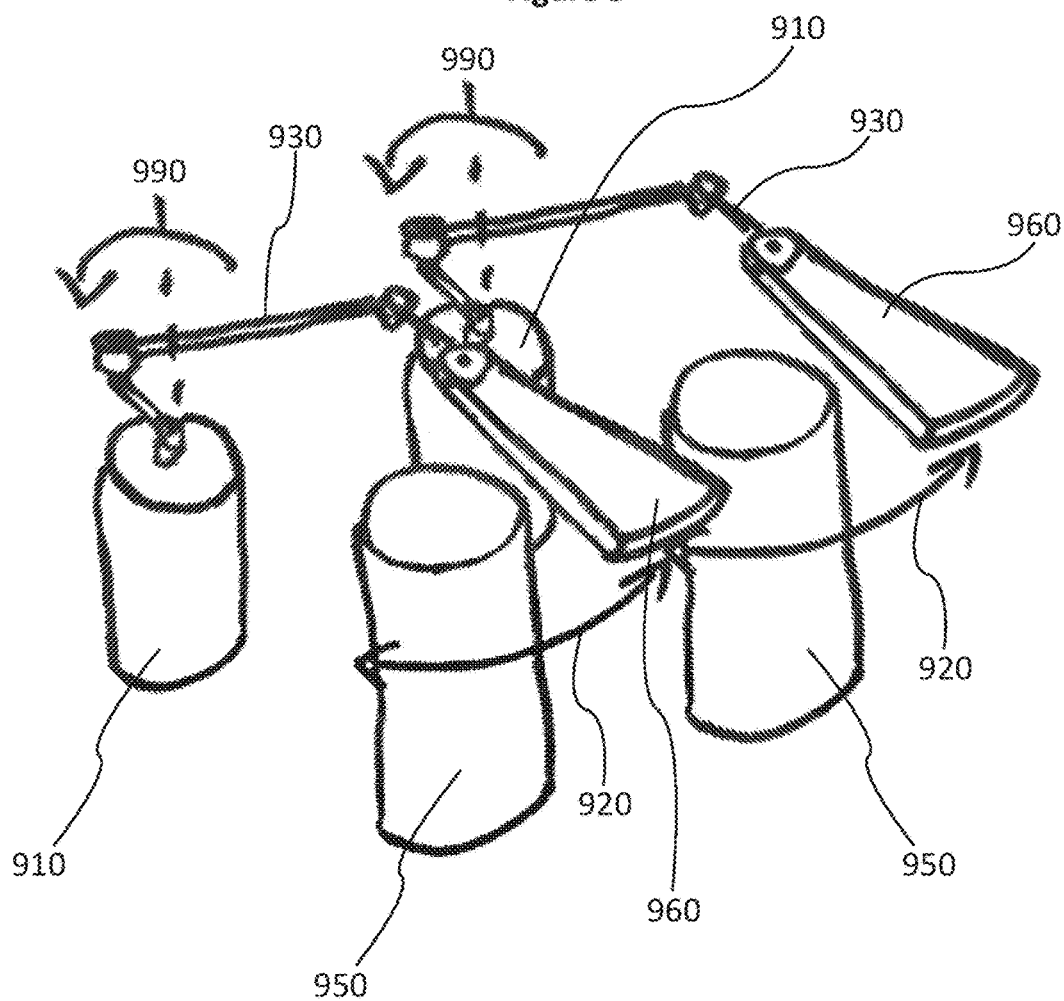
FIG. 9 is an example embodiment of an oscillating shutter system with a 4-bar linkage actuator.

Referring to FIG. 9 rotating 990 motors 910 are connected to the airflow interrupters 960 using links 930. The links 930 move 920 the airflow interrupters 960 to partially occlude the incoming air stream in the air stream path 950.

Figure 10:
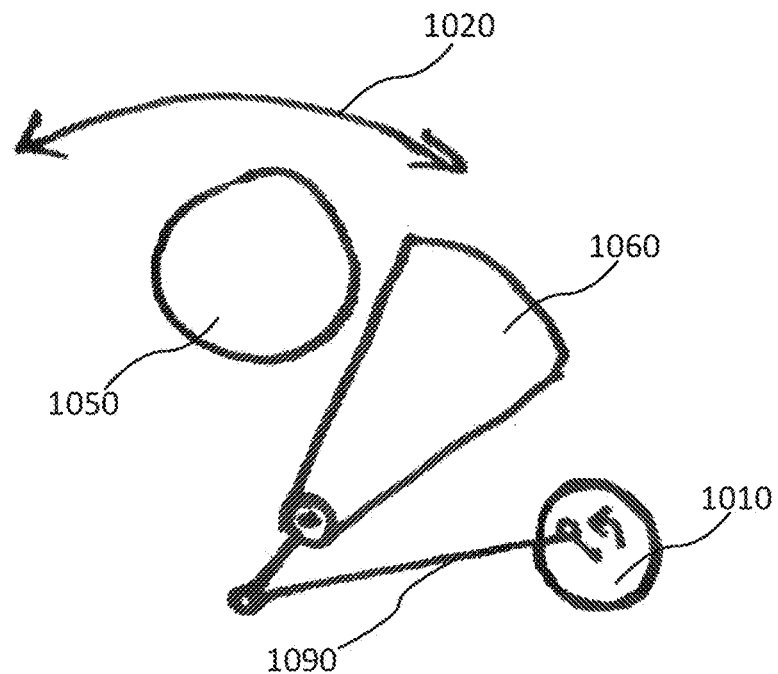
FIG. 10 is an example embodiment of an oscillating shutter system with a motor-crank actuator.

Referring to FIG. 10 a motor 1010 is connected to an airflow interrupter 1060 using links 1090. The links 1090 move 1020 the airflow interrupter 1060 to partially occlude the incoming air stream in the air stream path 1050.

Figure 11:
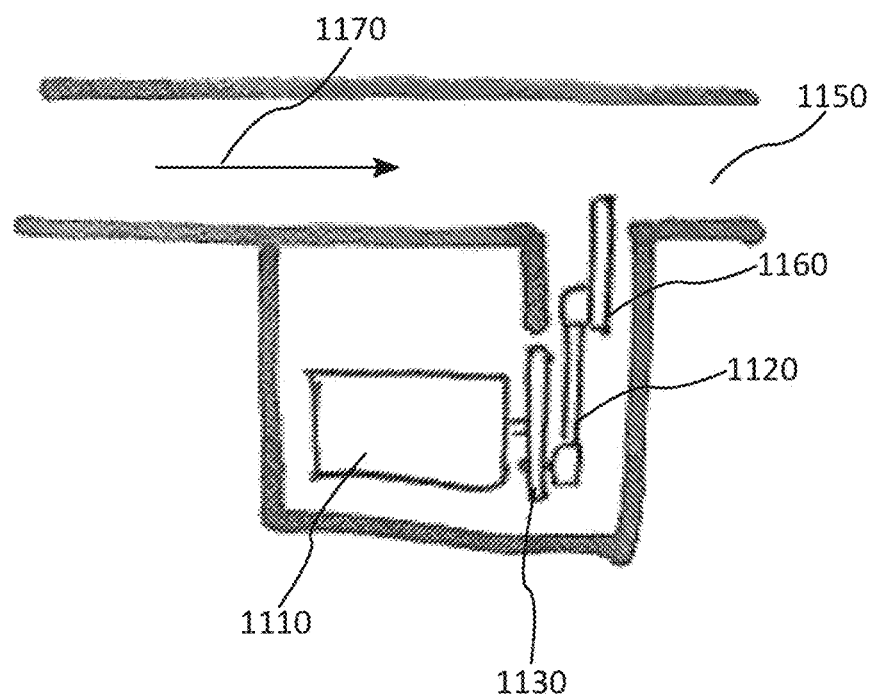
FIG. 11 is a side view of an example embodiment of an oscillating shutter system.

Referring to FIG. 11 a motor 1110 is connected to an airflow interrupter 1160 using a rotating disk 1130, that is in turn connected to a link 1120. The disk 1130 and link 1120 provide a linear motion to the airflow interrupter 1160. The motor 1110 moves the airflow interrupters 1160 backwards and forwards in a linear motion to partially occlude the incoming air stream 1170 in the air stream path 1150.

Figure 13:
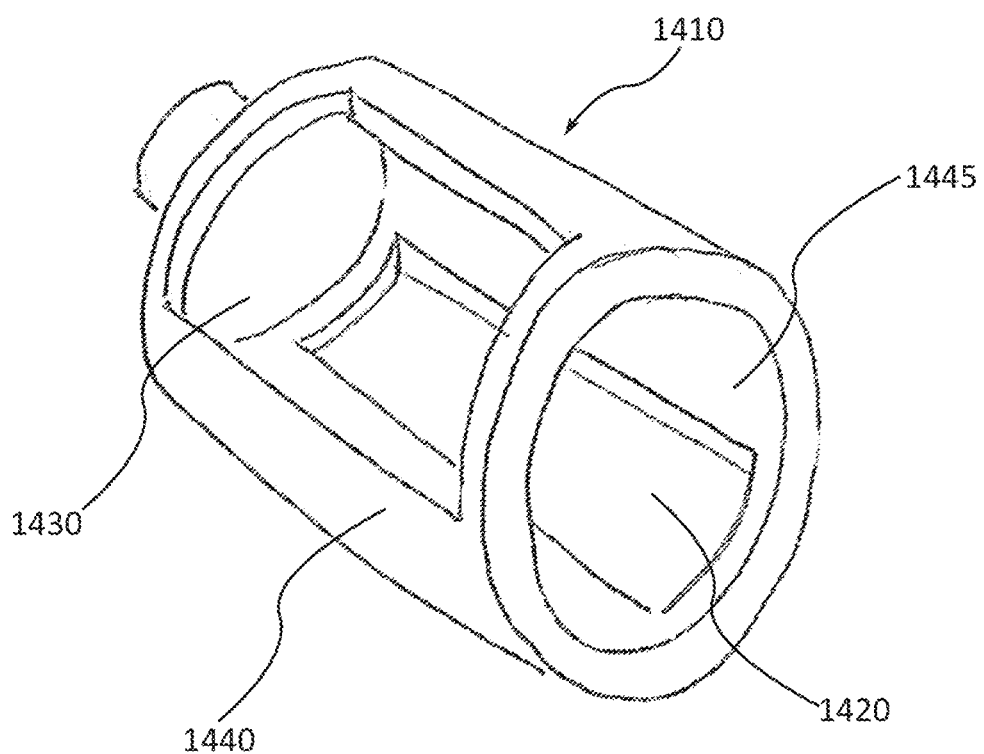
FIG. 13 is an example embodiment of a rotating barrel shutter.
Figure 14:
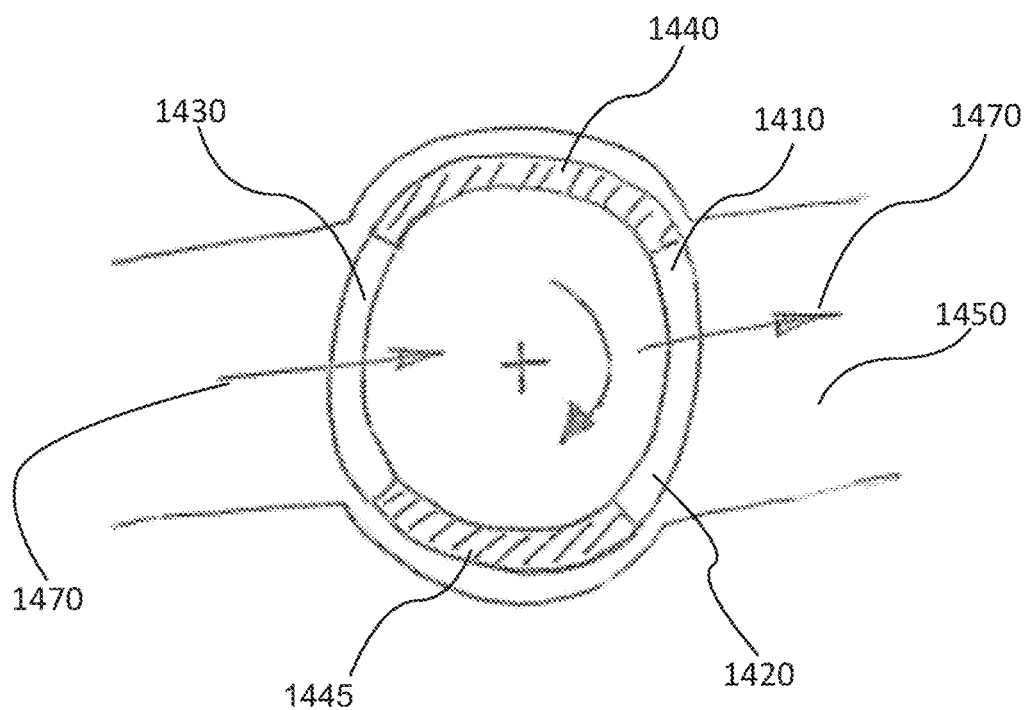
FIG. 14 is a cross section of the rotating barrel shutter inline in an air flow pipe.

Referring to FIGS. 13 and 14 a rotating barrel 1410 with alternating slots 1420, 1430 and solid portions 1440, 1445 to allow airflow could be utilised to partially occlude the incoming air stream 1470 in the air stream path 1450.

Figure 15:
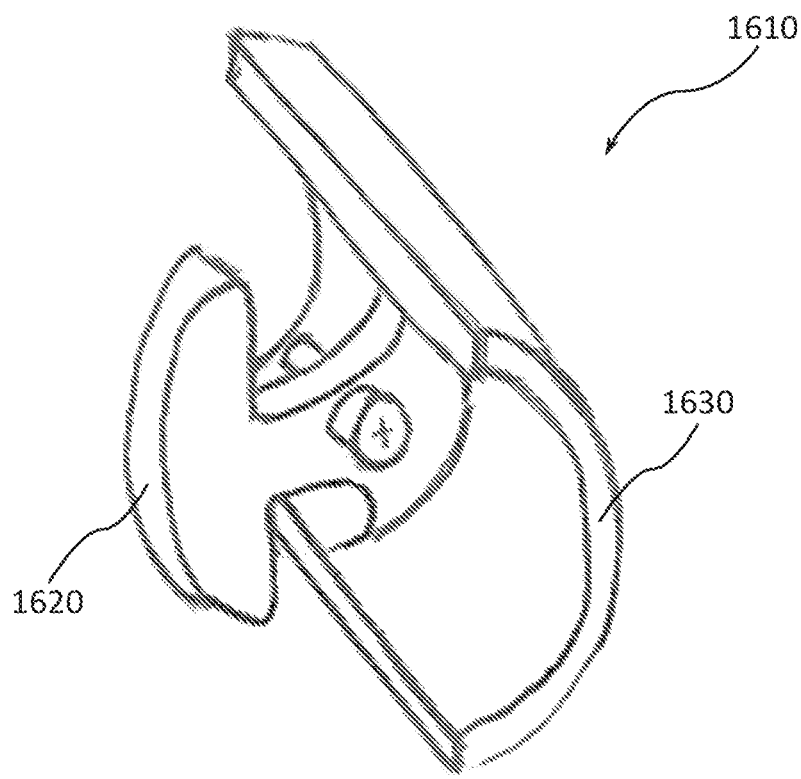
FIG. 15 is an example embodiment of a rotating partially blocking shutter.
Figure 16:
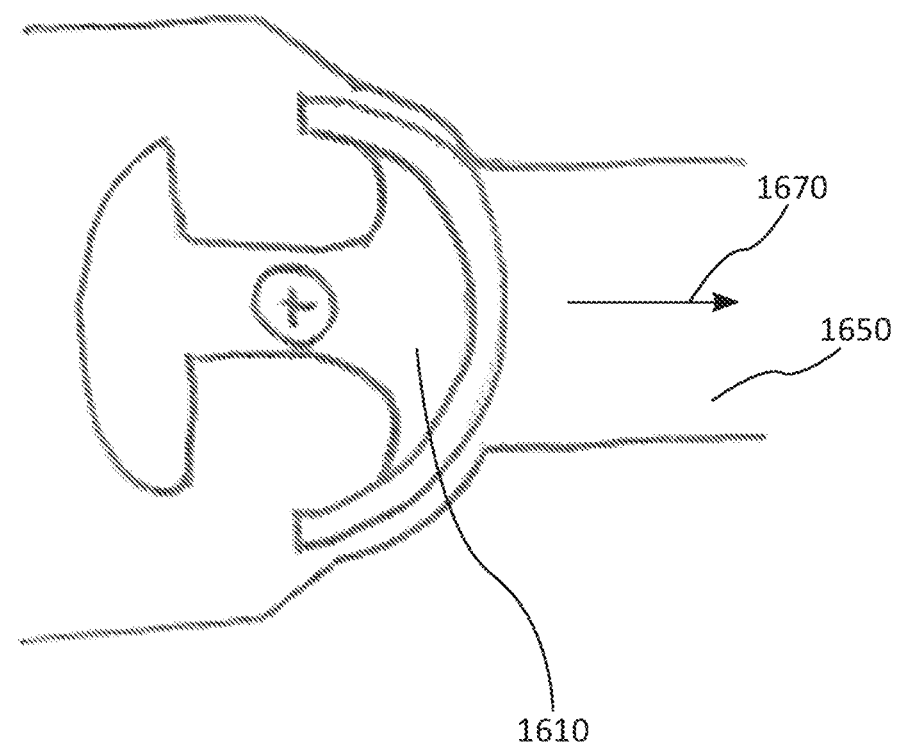
FIG. 16 is a cross section of the rotating partially blocking shutter inline in an air flow pipe.

Referring to FIGS. 15 and 16 a rotating shutter 1610 with alternating blocking 1630 and non-blocking 1620 portions to allow airflow could be utilised to partially occlude the incoming air stream 1670 in the air stream path 1650.

A single rotating barrel slide shutter system 1900, 2000, 2100 is illustrated by FIGS. 19A to 19D, 20A and 20B and 21A to 21C. A single rotating barrel slide shutter 1950, 2050, 2150 has slots 1955, 2055, 2155 and solid portions in the barrel. The barrel 1950, 2050, 2150 delivers pressure oscillations into the inhaled air stream 1970, 2070, 2170 entering the nose via a common manifold 1990, 2090, 2190. The air flowing to each nostril via first 1903, 2003, 2103 and second 1904, 2004, 2104 outlets.

Figure 12:
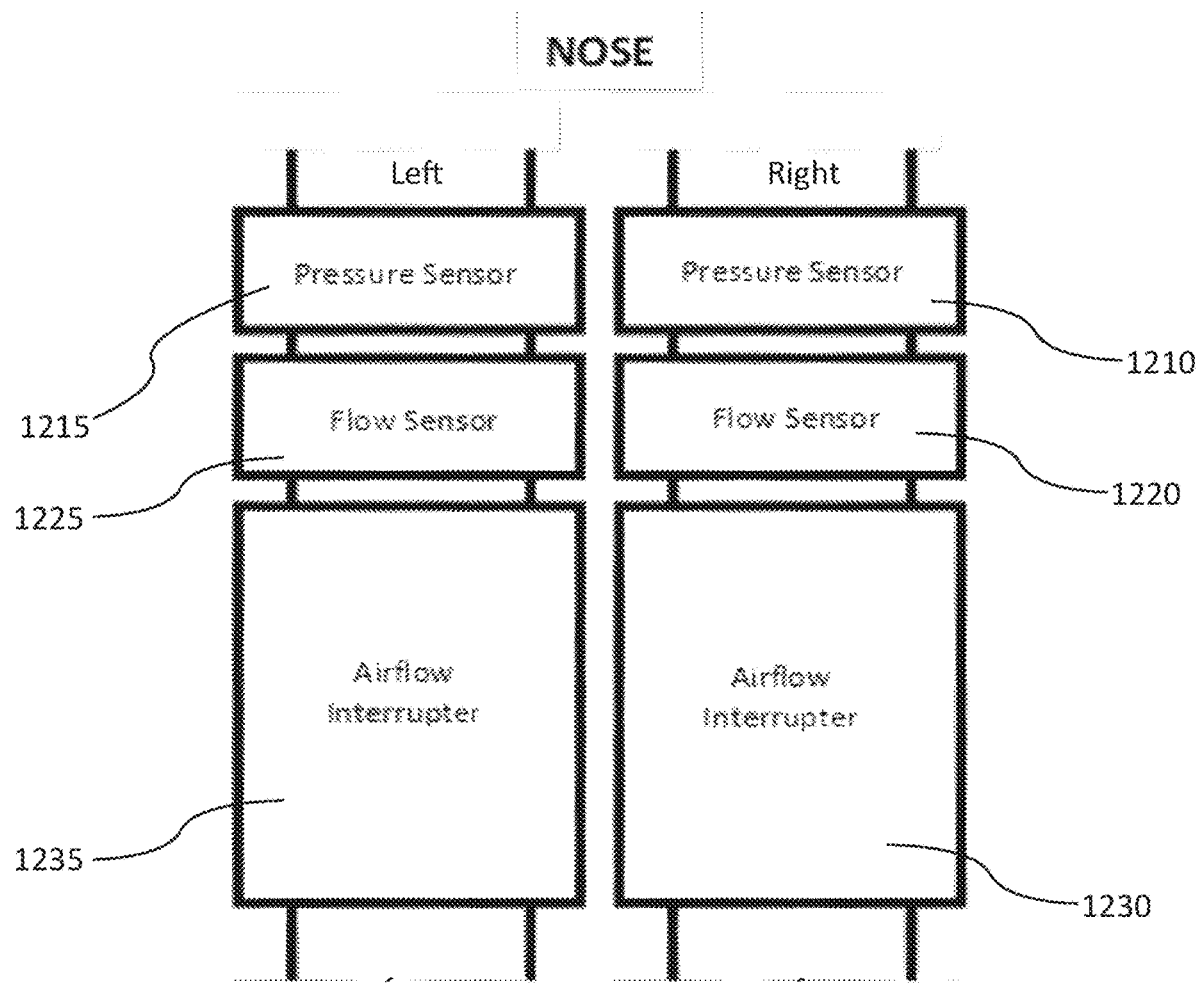
FIG. 12 is a diagram of the example sensors of the system.

Airflow shuttering could occur for just the inhalation breath phase or both inhalation and exhalation phases. Breath phase could be sensed via pressure sensors 1210, 1215 illustrated in FIG. 12 detecting low or high pressure during the inhalation or exhalation phases of breathing respectively. Alternatively, the system could use flow sensors 1220, 1225 to sense the flow. In a further alternative, if the rotating flow interrupter 1230, 1235 had slightly inclined blades, motor torque could be sensed to provide an indication of airflow direction.

Figure 17:
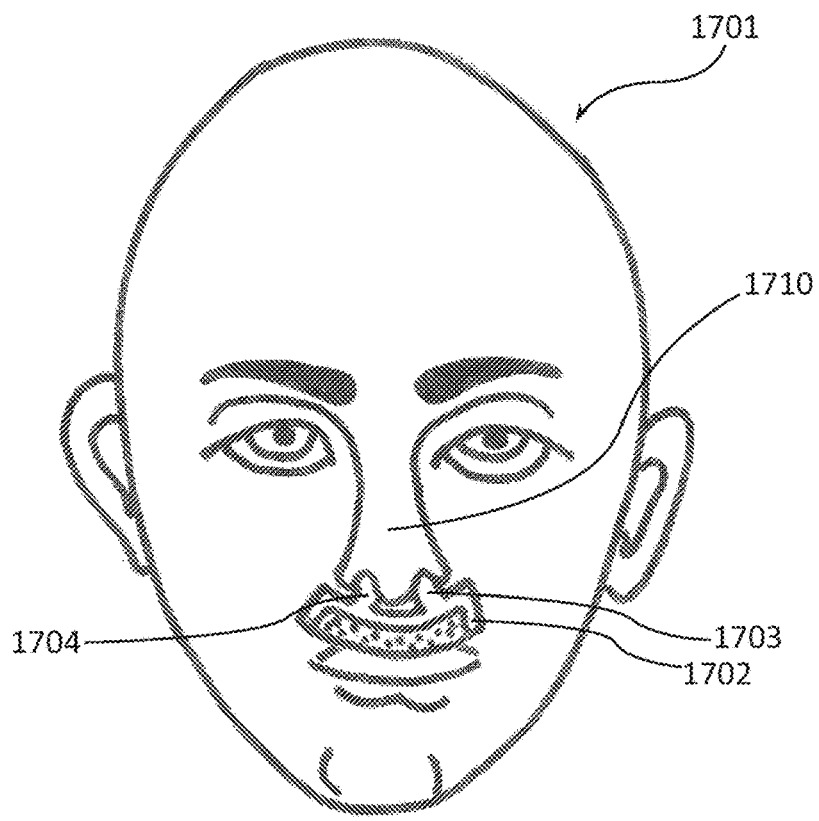
FIG. 17 is a front view of a person wearing an example embodiment of the apparatus.
Figure 18:
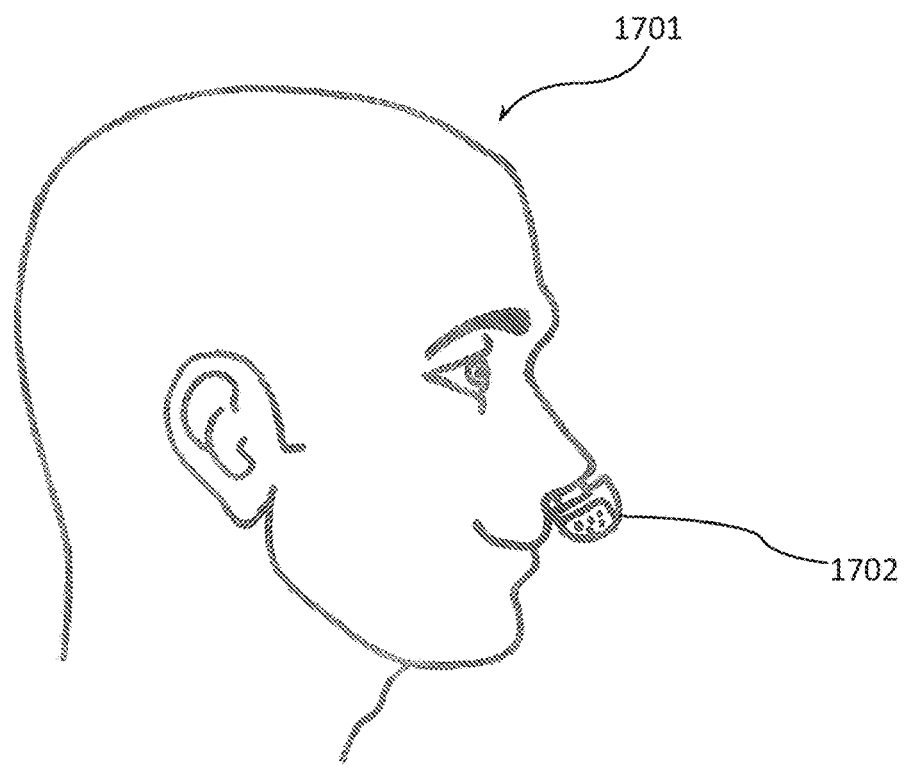
FIG. 18 is a side view of a person of FIG. 17 wearing an example embodiment of the apparatus.
Figure 19A:
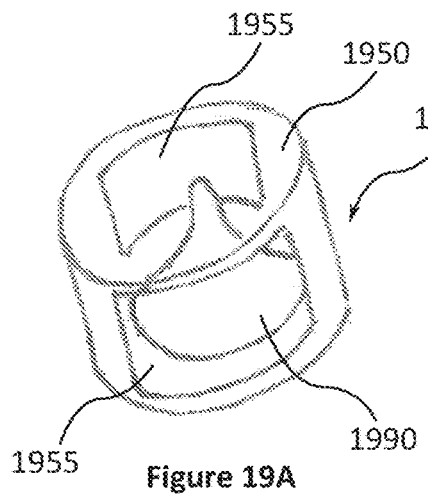
FIG. 19A is an example embodiment featuring a single rotating shutter, central air inlet/outlet port and side naris manifolds.
Figure 19C:
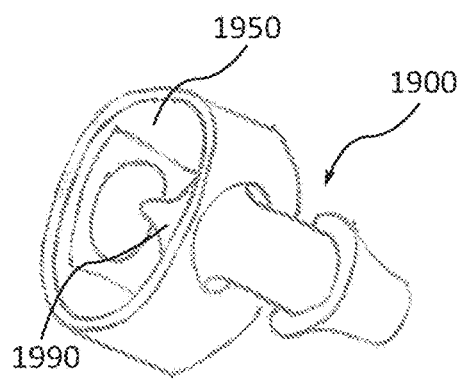
FIG. 19C is a pictorial view of housing with naris manifolds of an example embodiment featuring a single rotating shutter, central air inlet/outlet port and side naris manifolds.
Figure 19B:
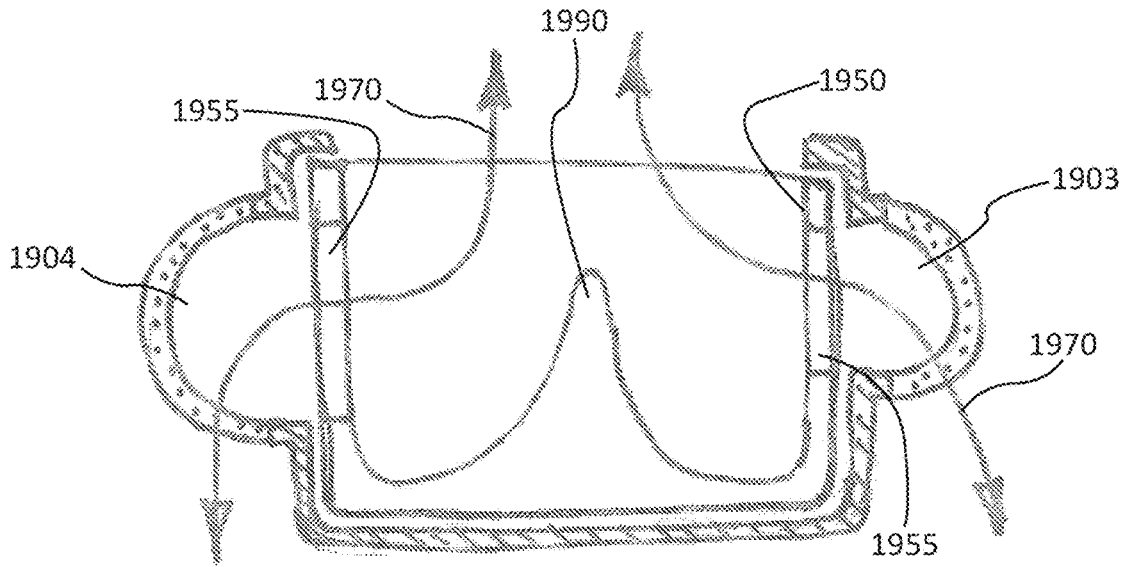
FIG. 19B is a sectional side view of FIG. 19A.
Figure 19D:
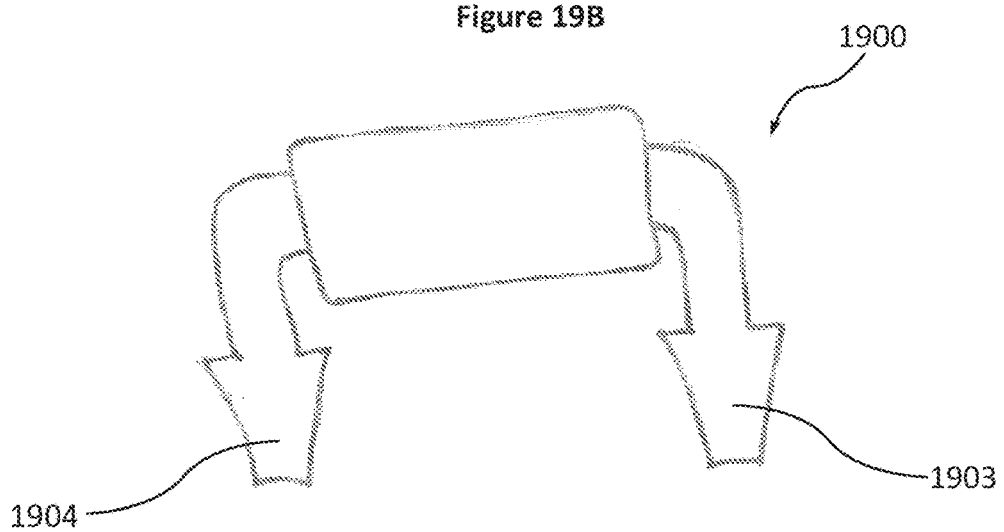
FIG. 19D is a top side view of FIG. 19C.
Figure 20A:
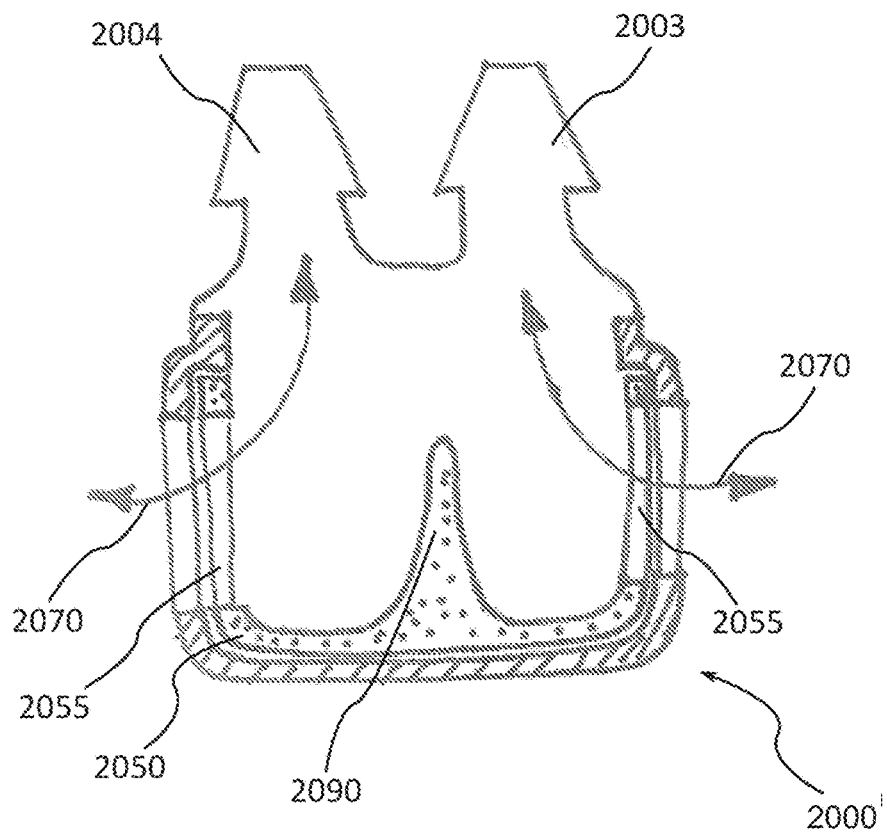
FIG. 20A is a sectional assembly side view showing air flow paths in an example embodiment featuring a single rotating shutter, central air inlet/outlet port and side naris manifolds.
Figure 20B:
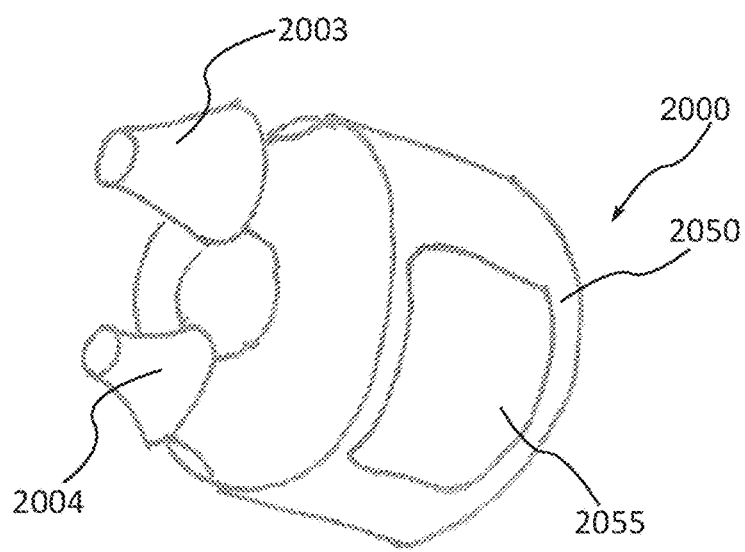
FIG. 20B is a pictorial view of the housing of FIG. 20A.
Figure 21A:
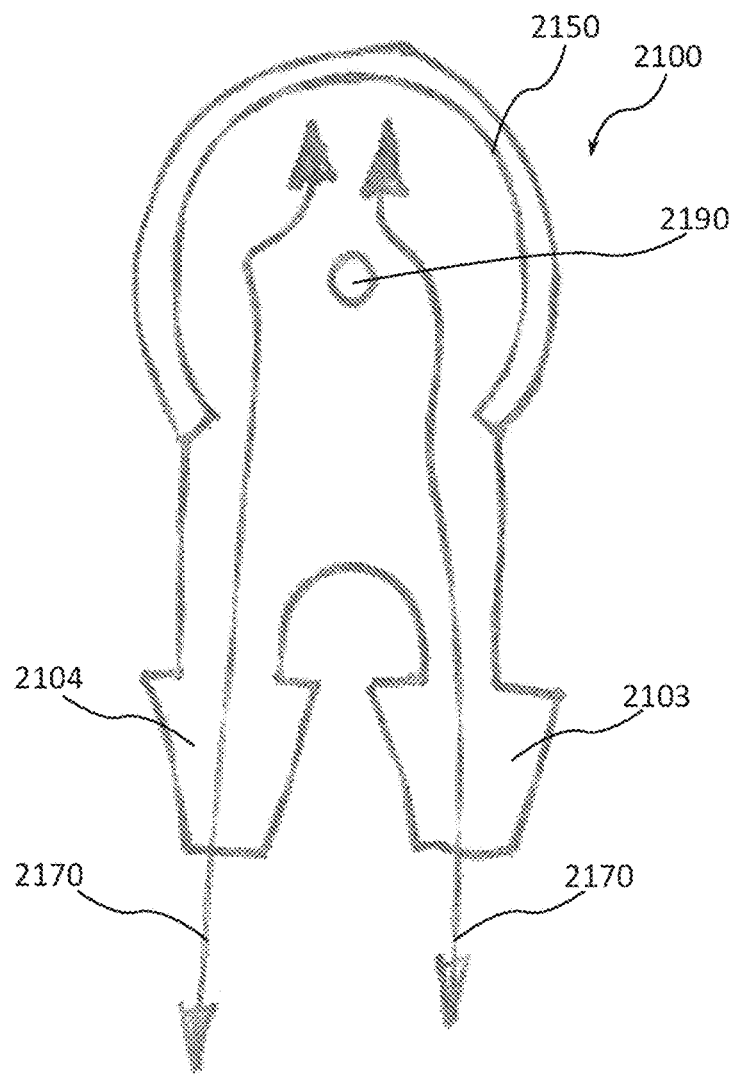
FIG. 21A is top view of an example embodiment featuring a single rotating shutter, central air inlet/outlet port and side naris manifolds.
Figure 21B:
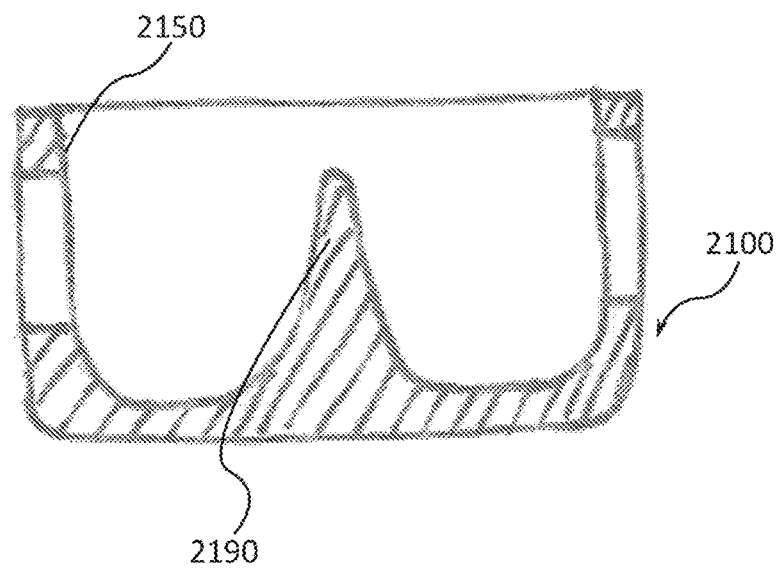
FIG. 21B is a sectional side view of FIG. 21A.
Figure 21C:
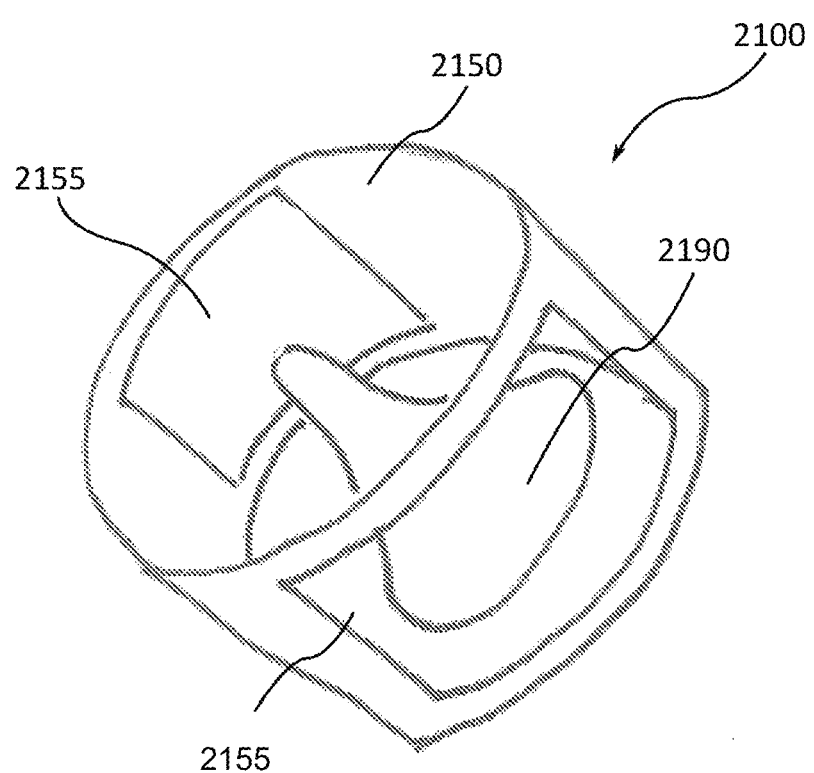
FIG. 21C is a pictorial view of the rotating shutter of FIG. 21A.

FIGS. 17 and 18 show the shutter system 1702 being used by a mammal/person 1701. Each naris 1703, 1704 receives a separate airflow.

Airflow shuttering could be applied to just one nostril, periodically alternating between either the right or left nostrils or simultaneously to both nostrils.

Shuttering of airflow could also be directed to a specific nostril depending upon the status of the user's nasal cycle where, for example, the paranasal sinuses within the congested nasal airway contain the highest NO levels. In a preferred embodiment airflow shuttering is applied to the congested nostril improving discharge of stored NO.

Periodically switching airflow shuttering between each side of the nose 1710 enables the NO concentration within the paranasal sinuses on one side to build up while the other is be discharged.

In one embodiment the device may be small enough that it could be worn discreetly under the nose and be battery powered.

Augmented iNO use assists in restoring sympathovagal balance and when combined with cyclically occluded air flow shear and pressure stresses also may potentially bring a multitude of therapeutic benefits that include:
1. Treating nasal congestion.
2. Improving airway hydration and mucociliary clearance to assist treating upper airway infection.
3. Post-operative recovery.
4. Pre-event build for high-performance sports.
5. Aid post-event muscle recovery.
6. Aiding sleep homeostasis in the elderly or insomniacs.
7. Aid sleep onset for shift workers.
8. Assist ventilation and blood oxygenation in COPD sufferers.
9. Prevent the onset of metabolic disease and assist in the management of Type-2 diabetes.
10. Assist blood pressure reduction.
11. Long-term benefits in reducing cardiovascular disease.
12. Treat traumatic brain injury.
13. Treat neurological diseases such as Alzheimer's and Parkinson's.

In an embodiment a method of stimulating airways of a mammal is provided by cyclically occluding a nasal air stream at a frequency rate between 50 Hz to 650 Hz.

Stimulating the airways of a mammal can improve nasal airflow by decongesting nasal obstruction in the mammal. Further stimulating the airways of a mammal can improve airway infection by enhancing airway hydration and mucociliary transport. Yet still further stimulating the airways of a mammal can improve the inhaled Nitric Oxide in the mammal.

When the mammal has two nares, a first naris and a second naris cyclically occluding the nasal air stream comprises simultaneously cyclically occluding the nasal air stream of both nares.

When the mammal has two nares, a first naris and a second naris and during a first mode of operation cyclically occluding the nasal air stream comprises cyclically occluding only the nasal air stream of the first naris. In this mode the nasal air stream to the second naris can be fully or partial restricted or unrestricted.

During the first mode the first naris is the congested naris and the second naris is the patent naris and cyclically occluding the nasal air stream comprises cyclically occluding only the nasal air stream of the second naris. In this mode the nasal air stream to the second naris can be fully or partial restricted or unrestricted.

During the second mode the second naris is the congested naris and the first naris is the patent naris. The change between the first mode and the second mode can be controlled by a controller.

The period of operation of the first mode or the second mode can be between 1 and 360 minutes, preferably between 1 and 15 minutes, more preferably between 1 and 5 minutes.

The nasal air stream can be cyclically occluded during both inhalation and exhalation or alternatively the nasal air stream can be cyclically occluded during inhalation only. Controlling the occlusion can be implemented by controlling an average percentage of obstruction of the nasal air stream. The average percentage of obstruction is between 5 and 95 percent.

Controlling the average percentage of obstruction of the nasal air stream includes controlling a percentage of time in a cycle in which the nasal air stream is at least partial obstructed and controlling a maximum percentage of obstruction of the nasal air stream. The maximum percentage of obstruction of the nasal air stream is between 5 and 95 percent.

In one embodiment the frequency rate is between 100 Hz to 450 Hz.

In one embodiment the mammal can be a human.

In an embodiment there is provided an apparatus for stimulating airways of a mammal, comprising a fluid connection to each of a first and second naris of the mammal, and an occluding device configured to cyclically occlude a nasal air stream within each fluid connection at a frequency rate between 100 Hz to 650 Hz.

Stimulating the airways of a mammal can improve nasal airflow by decongesting nasal obstruction in the mammal. Further stimulating the airways of a mammal can improve airway infection by enhancing airway hydration and mucociliary transport. Yet still further stimulating the airways of a mammal can improve the inhaled Nitric Oxide in the mammal.

Cyclically occluding the nasal air stream can comprise simultaneously cyclically occluding the nasal air stream of both nares.

The apparatus in a first mode cyclically occludes only the nasal air stream of the first naris and in the first mode the nasal air stream to the second naris can be unrestricted. Alternatively, in the first mode the nasal air stream to the second naris can be partially or fully restricted.

In the first mode the first naris can be the congested naris and the second naris can be the patent naris. The apparatus in a second mode can cyclically occludes only the nasal air stream of the second naris. In the second mode the nasal air stream to the second naris can be unrestricted. Alternatively, in the second mode the nasal air stream to the second naris can be partially or fully restricted.

Alternatively, in the second mode the second naris can be the congested naris and the first naris can be the patent naris. The change between the first mode and the second mode can be controlled by a controller.

The period of operation of the first mode or the second mode can be between 1 and 360 minutes, preferably between 1 and 15 minutes, more preferably between 1 and 5 minutes. The nasal air stream can be cyclically occluded during both inhalation and exhalation. Alternatively the nasal air stream can be cyclically occluded during inhalation only.

The apparatus can include a controller for controlling the occlusion by controlling an average percentage of obstruction of the nasal air stream. The average percentage of obstruction can be between 5 and 95 percent.

Controlling the average percentage of obstruction of the nasal air stream can include controlling a percentage of time in a cycle in which the nasal air stream is at least partial obstructed and controlling a maximum percentage of obstruction of the nasal air stream. The maximum percentage of obstruction of the nasal air stream can be between 5 and 95 percent.

In one embodiment the frequency rate is between 100 Hz to 450 Hz.

The mammal can be a human.

The apparatus can include a flow direction sensor and/or a pressure sensor. Further the apparatus can include a battery and can be configured to be worn under the nose. The apparatus can be a standalone device or can include an air supply device. The air supply device being selected from the group comprising CPAP, Bi-PAP, Auto-PAP and other assisted breathing devices.

The occluding device can be a linear slide shutter system including a liner solenoid actuator. Alternatively the occluding device can be a linear shutter system with crank actuator.

The occluding device can be a rotating shutter system. Alternatively, the occluding device can be a transverse rotating partially blocking shutter inline in the fluid connection. The transverse rotating partially blocking shutter can be a barrel and the barrel can include cut outs.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

REFERENCES

R1. Stewart M, Ferguson B, Fromer L. Epidemiology and burden of nasal congestion. Int J Gen Med. 2010; 3:37-45.
R2. Krouse J, Lund V, Fokkens W, Meltzer E Q. Diagnostic strategies in nasal congestion. Int J Gen Med. 2010; 3:59-67.
R3. Button B, Boucher R C. Role of mechanical stress in regulating airway surface hydration and mucus clearance rates. Respir Physiol Neurobiol. 2008;163(1-3):189-201.
R4. Button B, Picher M, Boucher R C. Differential effects of cyclic and constant stress on ATP release and mucociliary transport by human airway epithelia. J Physiol. 27 Apr. 2007; 580(2):577-92.
R5. Lundberg JON, Farkas-Szallasi T, Weitzberg E, Rinder J, Lidholm J, Anggaard A, et al. High nitric oxide production in human paranasal sinuses. Nat Med. 1995; 1(4):370-3.
R6. Lundberg J O. Nitric oxide and the paranasal sinuses. Anat Rec (Hoboken). 2008;291(11):1479-84.
R7. Maniscalco M, Sofia M, Pelaia G. Nitric oxide in upper airways inflammatory diseases. Inflamm Res. 2007; 56(2):58-69.
R8. Weitzberg E, Lundberg JON. Humming Greatly Increases Nasal Nitric Oxide. Am J Respir Crit Care Med. 2002; 166(2):144-5.
R9. Maniscalco M, Weitzberg E, SundbergJ, Sofia M, Lundberg J O. Assessment of nasal and sinus nitric oxide output using single-breath humming exhalations. Eur Respir J.
R10. Eby G A. Strong humming for one hour daily to terminate chronic rhinosinusitis in four days: A case report and hypothesis for action by stimulation of endogenous nasal nitric oxide production. Med Hypotheses. 2006;66(4):851-4.
R11. Prast H, Philippu A. Nitric oxide as modulator of neuronal function. Prog Neurobiol. 2001; 64(1):51-68.
R12. Kapás L, Fang J, Krueger J M. Inhibition of nitric oxide synthesis inhibits rat sleep. Brain Res. 1994; 664 (1):189-96.
R13. Toda N, Ayajiki K, Okamura T. Cerebral Blood Flow Regulation by Nitric Oxide: Recent Advances. Pharmacol Rev. 2009; 61(1):62-97.
R14. Scherer P S. Asthma, Viruses, and Nitric Oxide. Proc Soc Exp Biol Med. 1999; 220(3):123-32.
R15. Redington A E. Modulation of nitric oxide pathways: Therapeutic potential in asthma and chronic obstructive pulmonary disease. Eur J Pharmacol. 2006;533(1-3):263-76.
R16. Sanders S P, Proud D, Permutt S, Siekierski E S, Yachechko R, Liu M C. Role of nasal nitric oxide in the resolution of experimental rhinovirus infection. J Allergy Clin Immunol. 2004; 113(4):697-702.
R17. Djupesland P G, Chatkin J M, Qian W, Haight JSJ. Nitric oxide in the nasal airway: a new dimension in otorhinolaryngology. Am J Otolaryngol. 2001; 22(1):19-32.
R18. Lundberg JON, Farkas-Szallasi T, Weitzberg E, Rinder J, Lidholm J, Anggaard A, et al. High nitric oxide production in human paranasal sinuses. Nat Med. 1995; 1(4):370-3.
R19. Dickerson H. Nitric Oxide & Mouth Breathing: physiology you want to understand. Visions. 2017 Spring 2017:56.
R20. Lundberg JON, Weitzberg E. Nasal nitric oxide in man. Thorax. 1999;54(10):947-52.
R21. Lundberg J O, Settergren G, Gelinder S, Lundberg J M, Alving K, Weitzberg E. Inhalation of nasally derived nitric oxide modulates pulmonary function in humans. Acta Physiol Scand. 1996; 158(4):343-7.
R22. White D E, Bartley J, Nates R. Model demonstrates functional purpose of the nasal cycle. Biomed Eng Online. 2015;14(38):11.
R23. White D E, Bartley J, Shakeel M, Nates R J, Hankin RKS. Nasal airway responses to nasal continuous positive airway pressure breathing: An in-vivo pilot study. J Biomech. 2016; 49:1887-90.

R24. Zalewski P, Stomko J, Zawadka-Kunikowska M. Autonomic dysfunction and chronic disease. Br Med Bull. 2018; 128(1):61-74.

R25. Yang H. Sympathovagal Imbalance in Type 2 Diabetes—Role of Brainstem Thyrotropin-Releasing Hormone. In: Masuo K, editor. Type 2 Diabetes. Rijeka: InTech; 2013. p. 115-41.

R26. Shannahoff-Khalsa D. Lateralized rhythms of the central and autonomic nervous systems. Int J Psychophysiol. 1991; 11(3):225-51.

R27. Kleitman N. Basic rest-activity cycle-22 years later. Sleep. 1982; 5(4):311-7.

R28. Vinik A l, Murray G L. Autonomic Neuropathy is Treatable. US Endocrinology. 2008;4(2):3.

R29. Pal G, Agarwal A, Karthik S, Pal P, Nanda N. Slow yogic breathing through right and left nostril influences sympathovagal balance, heart rate variability, and cardiovascular risks in young adults. North American Journal of Medical Sciences. 2014; 6(3):145-51.

R30. Jella S A, Shannahoff-khalsa D S. The effects of unilateral forced nostril breathing on cognitive performance. Int J Neurosci. 1993;73(1-2):61-8.

R31. Shannahoff-Khalsa D S. Selective Unilateral Autonomic Activation: Implications for Psychiatry. CNS Spectrums. 2007; 12(08):625-34.

R32. Marshall R S, Basilakos A, Williams T, Love-Myers K. Exploring the Benefits of Unilateral Nostril Breathing Practice Post-Stroke: Attention, Language, Spatial Abilities, Depression, and Anxiety. The Journal of Alternative & Complementary Medicine. 2014; 20(3):185-94.

R33. Kishi T. Regulation of the sympathetic nervous system by nitric oxide and oxidative stress in the rostral ventrolateral medulla: 2012 Academic Conference Award from the Japanese Society of Hypertension. Hypertens Res. 2013; 36(10):845-51.

R34. Kimura A, Chiba S, Capasso R, Yagi T, Ando Y, Watanabe S, et al. Phase of nasal cycle during sleep tends to be associated with sleep stage. The Laryngoscope. 2013:n/a-n/a.

R35. Ko J-H, Kuo TBJ, Lee G-S. Effect of postural change on nasal airway and autonomic nervous system established by rhinomanometry and heart rate variability analysis. Am J Rhinol. 2008;22(2):159.

R36. Price A, Eccles R. Nasal airflow and brain activity: is there a link? The Journal of Laryngology & Otology. 2016:1-6.

R37. Klein R, Pilon D, Prosser S, Shannahoff-Khalsa D. Nasal airflow asymmetries and human performance. Biol Psychol. 1986; 23(2):127-37.

R38. Shannahoff-Khalsa D, Golshan S. Nasal cycle dominance and hallucinations in an adult schizophrenic female. Psychiatry Res. 2015; 226(1):289-94.

R39. Shannahoff-khalsa D S, Boyle M R, Buebel M E. The Effects of Unilateral Forced Nostril Breathing on Cognition. Int J Neurosci. 1991;57(3-4):239-49.

R40. Telles S, Nagarathna R, Nagendra H R. Breathing through a particular nostril can alter metabolism and autonomic activities. Indian J Physiol Pharmacol. 1994; 38(2):133-7.

R41. Dane S, Balci N. Handedness, eyedness and nasal cycle in children with autism. Int J Dev Neurosci. 2007; 25(4):223-6.

R42. Senol D, Ozan E, Tanisman S, Aydin N, Kirpinar I. P.1.b.006 Nasal cycle difference in schizophrenia: can it reflect the cerebral lateralization abnormality? Eur Neuropsychopharmacol. 2008;18, Supplement 4(0):5220.

R43. Kumaran E M. Alteration in nasal cycle rhythm as an index of the diseased condition: IntechOpen; 2017 2018. 11 p.

R44. Menzel L, Hess A, Bloch W, Michel O, Schuster K D, Gabler R, et al. Temporal nitric oxide dynamics in the paranasal sinuses during humming. J Appl Physiol. 2005; 98(6):2064-71.

R45. Maniscalco M, Weitzberg E, SundbergJ, Sofia M, Lundberg J O. Assessment of nasal and sinus nitric oxide output using single-breath humming exhalations. Eur Respir J.

R46. Shusterman D J, Jansen K, Weaver E M, Koenig J Q. Documentation of the nasal nitric oxide response to humming: methods evaluation. EurJ Clin Invest. 2007; 37(9):746-52.

R47. Eby G A. Strong humming for one hour daily to terminate chronic rhinosinusitis in four days: A case report and hypothesis for action by stimulation of endogenous nasal nitric oxide production. Med Hypotheses. 2006; 66(4):851-4.

R48. Cairns A, Bogan R. The SinuSonic: reducing nasal congestion with acoustic vibration and oscillating expiratory pressure. Medical devices (Auckland, NZ). 2019; 12:305-310.

The invention claimed is:

1. A method of stimulating nasal airways of a mammal wherein the mammal has two nares of a mammal, and a first naris and a second naris, the method comprising:
   providing a fluid connection for each of the first and second naris for a nasal airstream to enter each of the first and second naris of the mammal;
   using an occluding device to cyclically occlude a nasal air stream within each fluid connection to cause pressure oscillations, said cyclic occlusion at a frequency rate between 50 Hz to 650 Hz to deliver pressure oscillations into the air stream entering the respective first or second naris, thereby simulating humming, which stimulates discharge of Nitric Oxide (NO) from a paranasal sinus connected to the nasal airway of the respective first or second naris into the nasal airway of the respective first or second naris so as to improve nasal airflow by reducing congestion of the respective first or second naris,
   wherein during a first mode cyclically occluding the nasal air stream comprises cyclically occluding only the nasal air stream of the first naris,
   wherein during a second mode cyclically occluding the nasal air stream comprises cyclically occluding only the nasal air stream of the second naris, and
   wherein change between the first mode and the second mode is controlled by a controller.

2. The method of claim 1 wherein stimulating the airways of a mammal improves the inhaled Nitric Oxide into an inhaled nasal airstream.

3. The method of claim 1, wherein during the first mode the nasal air stream to the second naris is restricted.

4. The method of claim 1, wherein during the first mode the first naris is the congested naris and the second naris is the patent naris.

5. The method of claim 1, wherein during the second mode the second naris is the congested naris and the first naris is the patent naris.

6. The method of claim 1, wherein the period of operation of the first mode or the second mode is between 1 and 15 minutes.

7. The method of claim 1, wherein the nasal air stream is cyclically occluded during inhalation only.

8. The method of claim 1, the method including controlling the occlusion by controlling an average percentage of obstruction of the nasal air stream.

9. The method of claim 8, wherein the average percentage of obstruction is between 5 and 95 percent.

10. The method of claim 8, wherein controlling the average percentage of obstruction of the nasal air stream includes controlling a percentage of time in a cycle in which the nasal air stream is at least partial obstructed and controlling a maximum percentage of average obstruction of the nasal air stream.

11. The method of claim 10, wherein the maximum percentage of average obstruction of the nasal air stream is between 5 and 95 percent.

12. The method of claim 1, wherein the frequency rate is between 100 Hz to 450 Hz.

13. The method of claim 1, wherein during a third mode cyclically occluding the nasal air stream comprises simultaneously cyclically occluding the nasal air stream of both nares and wherein the change between the first, second and third modes is controlled by the controller.

14. The method of claim 1 comprising sensing airflow pressure for the controller to use in changing between the first mode and the second mode.

15. The method of claim 1 wherein said stimulation is performed during inhalation through the first or second naris to increase the inhaled Nitric Oxide in an inhaled nasal airstream.

16. The method of claim 1 wherein said stimulation is performed during inhalation through the first or second naris to cause Nitric Oxide to be discharged from the paranasal sinuses into an inhaled nasal airstream.

17. An apparatus for stimulating nasal airways of a mammal, comprising:
a fluid connection to each of a first and second naris of the mammal for a nasal air stream to the respective first and second naris;
an occluding device configured to cyclically occlude a nasal air stream within each fluid connection at a frequency rate between 100 Hz to 650 Hz to deliver pressure oscillations into the air stream entering the respective first or second naris, thereby simulating humming, which stimulates discharge of Nitric Oxide (NO) from a paranasal sinus connected to the nasal airway of the respective first or second naris into the nasal airway of the respective first or second naris so as to improve nasal airflow by reducing congestion of the respective first or second naris; and
a controller,
wherein the apparatus in a first mode cyclically occludes only the nasal air stream of the first naris,
wherein the apparatus in a second mode cyclically occludes only the nasal air stream of the second naris,
wherein change between the first mode and the second mode is controlled by the controller.

18. The apparatus of claim 17, wherein the period of operation of the first mode or the second mode is between 1 and 15 minutes.

19. The apparatus of claim 17, wherein the nasal air stream is cyclically occluded during inhalation only.

20. The apparatus of claim 17, further including a flow direction sensor.

21. The apparatus of claim 17, further including a pressure sensor.

22. The apparatus of claim 17, wherein the apparatus includes a battery and is configured to be worn under the nose.

23. The apparatus of claim 17, wherein the apparatus is a standalone device.

24. The apparatus of claim 17, wherein the occluding device is a linear slide shutter system including a linear solenoid actuator.

25. The apparatus of claim 17, wherein the occluding device is a linear shutter system with crank actuator.

26. The apparatus of claim 17, wherein the occluding device is a rotating shutter system.

27. The apparatus of claim 17, wherein the occluding device is a transverse rotating partially blocking shutter inline in the fluid connection.

28. The apparatus of claim 27, wherein the transverse rotating partially blocking shutter is a barrel and the barrel include cut outs.

* * * * *